US00PP19625P2

(12) United States Plant Patent
Cho

(10) Patent No.: US PP19,625 P2
(45) Date of Patent: Jan. 13, 2009

(54) ***COLOCASIA* PLANT NAMED 'MAUI MAGIC'**

(50) Latin Name: *Colocasia esculenta*
Varietal Denomination: MAUI MAGIC

(76) Inventor: John Cho, P.O. Box 269, 424 Mauna Pl., Kula, HI (US) 96790

( * ) Notice: Subject to any disclaimer, the term of this patent is extended or adjusted under 35 U.S.C. 154(b) by 0 days.

(21) Appl. No.: 11/891,593

(22) Filed: Aug. 13, 2007

(51) Int. Cl.
*A01H 5/00* (2006.01)

(52) U.S. Cl. ..... Plt./226

(58) Field of Classification Search ..... Plt./373
See application file for complete search history.

*Primary Examiner*—Wendy C. Haas

(57) ABSTRACT

A new cultivar of cultivar of *Colocasia* plant named 'MAUI MAGIC' that is characterized by a combination of large ruffled glossy green-grey to purple leaves, multiple shoots and purple petioles. In combination these characteristics distinguish 'MAUI MAGIC' from all other varieties of *Colocasia* known to the inventor.

5 Drawing Sheets

Genus: *Colocasia.*
Species: *esculenta.*
Denomination: 'MAUI MAGIC'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'MAUI MAGIC'.

*Colocasia* is a tuberous rooted perennial which is native to tropical Asia and Polynesia. It grows to 1.5 m–2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'MAUI MAGIC' is the product of a formal breeding program of the University of Hawaii, Kula. The purpose of the breeding program was to develop new commercial varieties by combining attributes not found in current commercially available varieties.

'MAUI MAGIC' is a seedling selection from the controlled pollination between the female parent '2001-51' (unpatented) and male parent '2000-177' (unpatented). The female parent '2001-51' was selected from the progeny of a genetic cross between breeding hybrid line '2000-28' (unpatented) and breeding hybrid line '2000-132' (unpatented). The male parent '2000-177' was selected from a genetic cross between *Colocasia* 'Putih' (unpatented) and *Colocasia* 'PH21' (unpatented). Initially designated as '2005-32', 'MAUI MAGIC' was derived from a single plant selected in 2005.

The new variety 'MAUI MAGIC' has very large glossy green-grey purple leaves that are ruffled in texture with undulating leaf margins. 'MAUI MAGIC' produces uniform light to dark purple petioles. The leaves are one-third to one-half times larger than its male parent and two to three times larger than its female parent. The male parent, '2000-177', exhibits smaller glossy green leaves with irregular purple blotches with a smooth margin. The petioles of '2000-177' are a light green to a light purple color with dark purple streaks. The female parent, '2001-51' exhibits smaller green leaves with a purple spot on the upper leaf surface at the point of leaf and petiole attachment and a smooth margin. The petioles of '2001-51' are of a light green color. Finally, 'MAUI MAGIC' has an overall height of 5 to 6 feet compared to '2001-51' which grows to 1 to 2 feet in height.

The closest comparison commercial variety known to the inventor is *Colocasia* 'Fontanesii' (unpatented). 'MAUI MAGIC' produces glossy green-grey to purple leaves that are ruffled in texture and has undulating leaf margin compared to 'Fontanesii' which exhibits a glossy green smooth leaf with a smooth margin. 'MAUI MAGIC' produces a uniform light to dark purple petioles compared with 'Fontanesii' that exhibit petioles with dark purple color. 'MAUI MAGIC' produces leaves which are about one-fourth larger than the leaves of 'Fontanesii', giving 'MAUI MAGIC' a full appearance. 'MAUI MAGIC' produces secondary lateral shoots that are closely attached to the mother plant as compared with 'Fontanesii' which produces secondary lateral shoots on long stolons.

Asexual propagation of 'MAUI MAGIC' began in 2005 in Hawaii by the inventor using huli propagation whereby the apical shoots are separated from the plant by cutting the shoot at the top of the corm immediately above the newest leaf scar and planted. Evaluation in field and pot studies have shown the unique features of 'MAUI MAGIC' to be stable, uniform, and to be reproduced true to type in successive generations of asexual propagation.

SUMMARY OF THE INVENTION

The following traits have been repeatedly observed and represent the distinguishing characteristics of the new *Colocasia* variety named 'MAUI MAGIC'. In combination these traits set 'MAUI MAGIC' apart from all other varieties of *Colocasia* known to the inventor. 'MAUI MAGIC' has not been tested under all possible conditions and phenotypic differences may be observed with variations in environmental, climatic and cultural conditions, however, without any variance in genotype:

1. 'MAUI MAGIC' exhibits large ruffled heart-shaped leaves.
2. The leaves of 'MAUI MAGIC' range in color from green-grey to purple.
3. The surface of the leaves of 'MAUI MAGIC' is glossy.
4. 'MAUI MAGIC' has purple petioles.

BRIEF DESCRIPTION OF THE DRAWINGS

The accompanying color drawings

Figure 1:
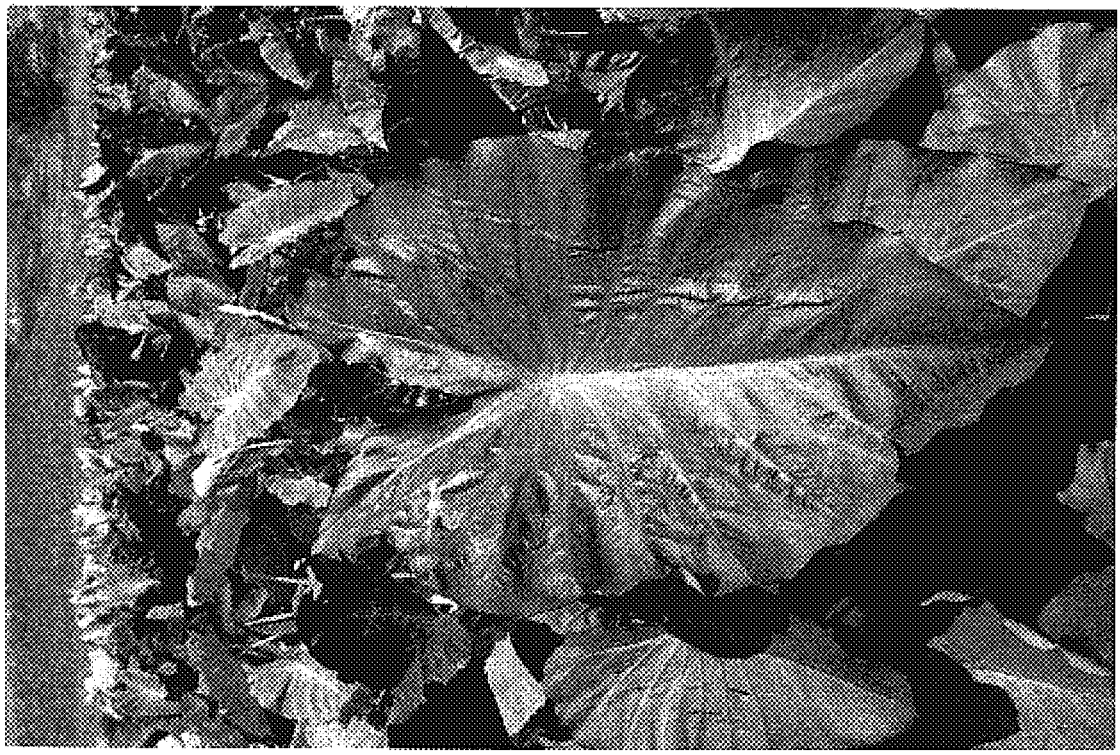
FIGS. 1 to 5 illustrate the overall appearance of 'MAUI MAGIC' showing the colors as true as it is reasonably possible to obtain in colored reproductions of this type. Colors in the drawing may differ from the color values cited in the detailed botanical description, which accurately describe the actual colors of the new variety 'MAUI MAGIC'.

The drawing labeled as FIG. 1 shows the upper surface of a slightly ovate sagittate 'MAUI MAGIC' mature leaf blade with a deep 115 degree to 145 degree acute angle sinus between lobes. It also shows the piko i.e. point of attachment of petiole to the lamina. Lamina is a glossy dark green with light-purple venation.

Figure 2:
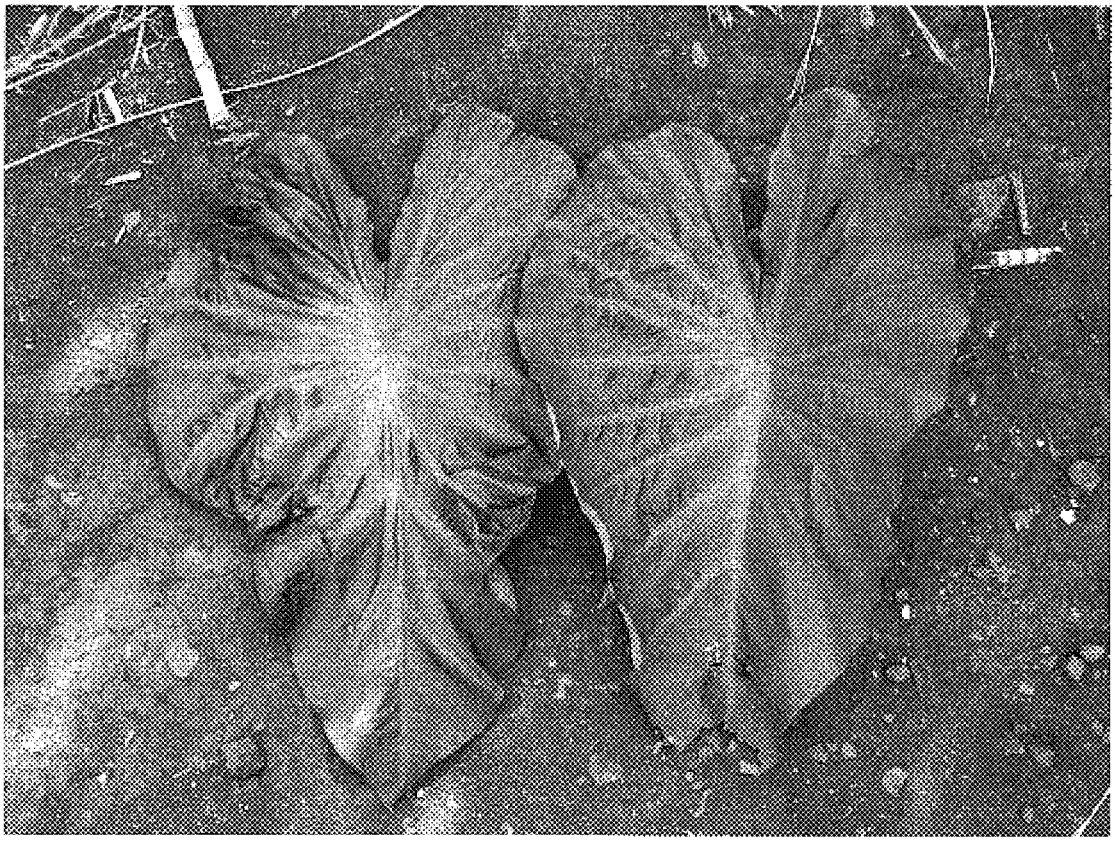

The drawing labeled FIG. 2 compares a mature leaf and recently unfurled young leaf that is purple-green in color with light-purple venation.

Figure 3:
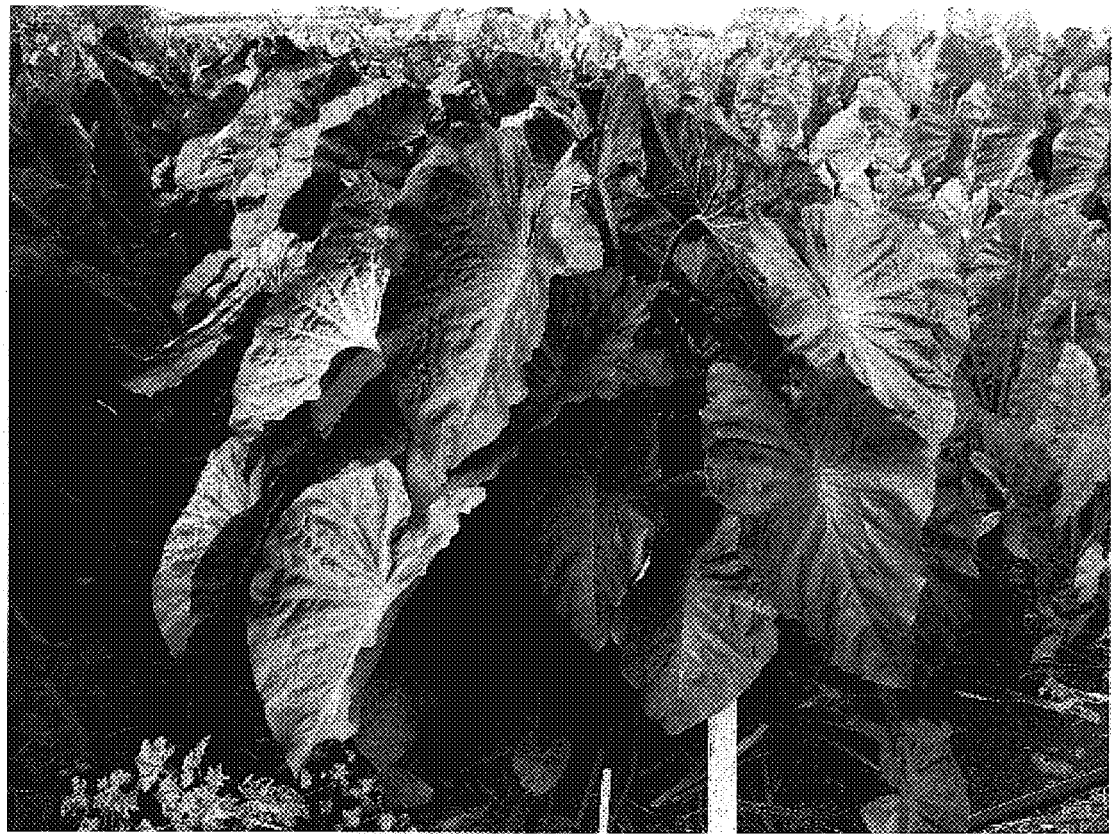

The drawing labeled as FIG. 3 shows a side view of a mature plant of 'MAUI MAGIC'.

Figure 4:
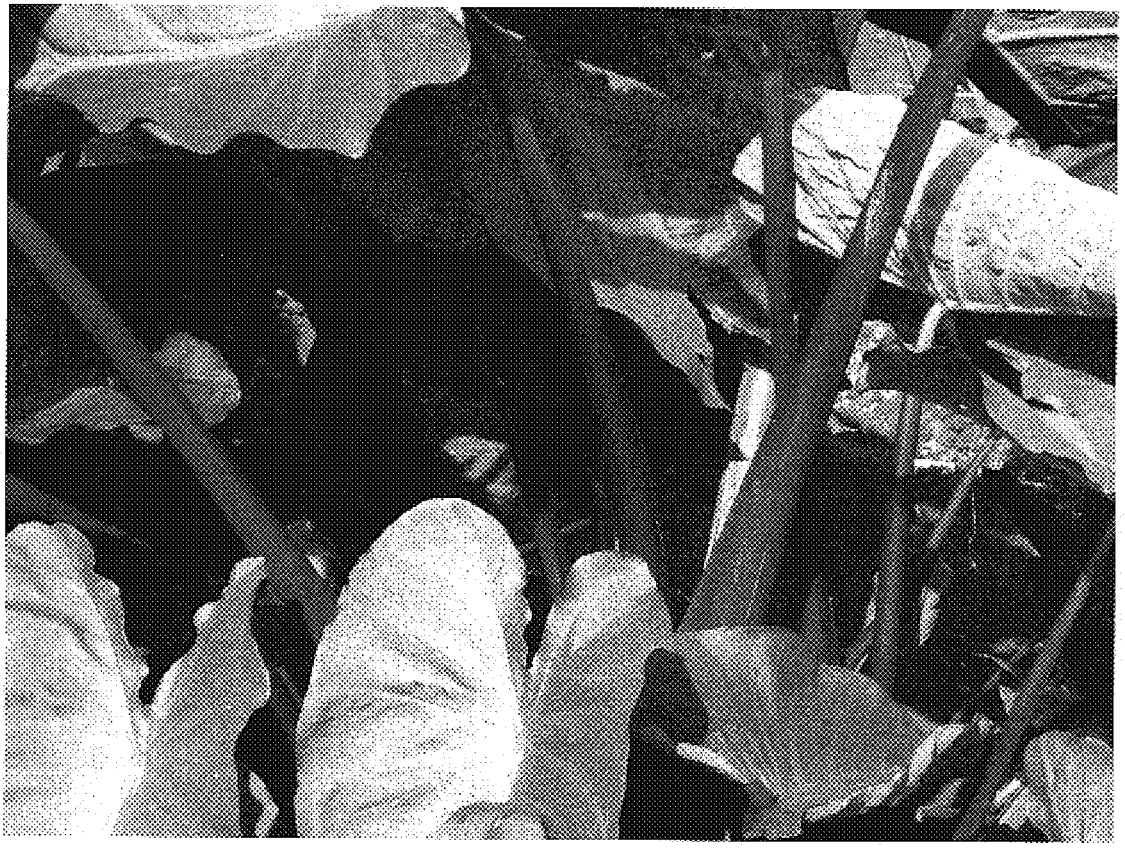

The drawing labeled as FIG. 4 shows the violet-purple petioles of 'MAUI MAGIC'.

Figure 5:
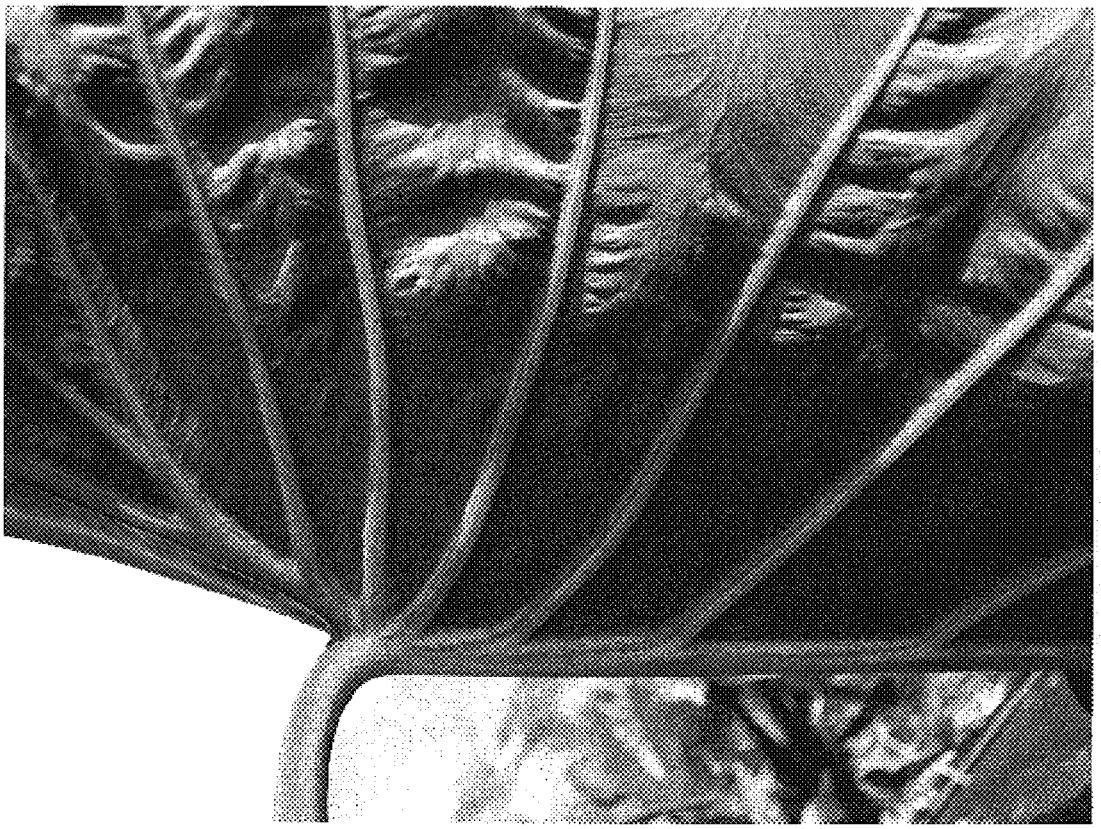

The drawing labeled as FIG. 5 shows the underside of a mature leaf of 'MAUI MAGIC' with the dark green lamina and slightly purple venation.

All drawings have been made from plants which were approximately 5 months old from a division and which have been grown out-of-doors. No growth regulators have been applied.

BOTANICAL DESCRIPTION OF THE PLANT

The following is a detailed description of the new *Colocasia* plant named 'MAUI MAGIC'. Data was collected from plants that were 3–6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia.*

Botanical classification:
Genus: *Colocasia.*
Species: *esculenta.*
Denomination: 'MAUI MAGIC'.
Common name: Taro or elephant ears.
Plant use: Food, container or landscape plant.
Cultural requirements: Cultural requirements are well draining soil or growing media, full sun to partial shade.
Root system: Fibrous.
Plant vigor: Vigorous.
Parentage:
*Female parent.*—'2001-15'.
*Male parent.*—'2000-177'.
Plant description: The plant has 5–6 suckers closely attached to the mother plant. A "mother plant" is the plant material which is first introduced into the soil to begin production. Typically, this plant material contains part of the huli and 2–3 leaf blades. This produces a "mother corm" which produces lateral shoots called 'cormels' which give rise to daughter plants. Daughter plants begin to appear above soil level about 2–3 months after planting of the mother plant.
Plant dimensions:
*Height.*—1220 mm to 1525 mm.
*Width.*—125 mm to 160 mm.
Plant hardiness: USDA Zone 7b.
Propagation: Propagation is accomplished by huli propagation.
Time to develop daughter plants: Appear above soil around 2–3 months after planting.
Crop time: 6–10 weeks.
Pest or disease susceptibility and resistance: No more or less susceptible to disease or pests than other cultivars of *Colocasia.*
Foliage:
*Number.*—On average, a 4–10 month old mother plant maintains 6–7 functional leaves at a time; each new leaf is produced approximately every 10 days until the corm matures.
*Petioles.*—Length: Up to 126.9 cm in length. Width: 10 mm (just below attachment to lamina); 20 mm (at the upper sinus); 28 mm (at the middle of the sinus). Color: N77B towards corm, N77A towards leaf, N77B at point of attachment. Sap color: Colorless.
*Leaf.*—Dimensions at maturity (5–6 months old): 70.7 cm in length and 47.7 cm in width. Aspect: Erect with apex down. Shape: Sagittate, slightly ovate lamina. Margins: Entire, undulating. Apex: Pointed. Base: Peltate, deep 115 degree to 145 degree acute angle sinus between lobes. Lamina appendages: Absent. Attachment: Piko, small in size. Leaf sheaf: Open. Texture: Glossy. Leaf color (abaxial surface): 136A when young changing to 138B and 135B when older. Lear color (adaxial surface): 148A. Venation: Palmate. Veins: Three principal veins radiating from the piko. The largest a midrib extending from the piko to the tip of the lamina with up to 10 pairs of secondary veins radiating from it. Vein color (adaxial surface): 77B. Vein color (abaxial surface): 76B.
Flowers and reproductive organs: No flowers have been produced to date.

What is claimed is:

1. A new and distinct cultivar of *Colocasia* plant named 'MAUI MAGIC' as described and illustrated herein.

* * * * *

UNITED STATES PATENT AND TRADEMARK OFFICE

CERTIFICATE OF CORRECTION

PATENT NO. : PP19,625 P2
APPLICATION NO. : 11/891593
DATED : January 13, 2009
INVENTOR(S) : John Cho It is certified that error appears in the above-identified patent and that said Letters Patent is hereby corrected as shown below:

On Column 1, line 1, please insert the following header and paragraph:

--Statement of Government Interest

This invention was made with Government support under Grant No. 2005-31100-06015/HAW00948H awarded by the U.S. Department of Agriculture. The Government has certain rights in this invention.--

Signed and Sealed this
Seventeenth Day of May, 2011

David J. Kappos

David J. Kappos
*Director of the United States Patent and Trademark Office*